United States Patent [19]

Sauter et al.

[11] Patent Number: 5,032,616
[45] Date of Patent: Jul. 16, 1991

[54] 4-SUBSTITUTED CYCLOHEXYLAMINE DERIVATIVES, FUNGICIDES CONTAINING THESE AND A METHOD OF CONTROLLING FUNGI

[76] Inventors: Hubert Sauter, 20 Neckarpromenade, 6800 Mannheim 1; Matthias Zipplies, 1 Kastanienweg, 6945 Hirschberg; Norbert Goetz, 25 Schoefferstrasse, 6520 Worms 1; Eberhard Ammermann, 3 Sachsenstrasse, 6700 Ludwigshafen; Ernst-Heinrich Pommer, 7 Berliner Platz, 6703 Limburgerhof, all of Fed. Rep. of Germany

[21] Appl. No.: 90,761

[22] Filed: Aug. 28, 1987

[30] Foreign Application Priority Data

Sep. 5, 1986 [DE] Fed. Rep. of Germany ....... 3630344

[51] Int. Cl.$^5$ .................... A01N 33/04; C07C 211/35; C07C 211/40
[52] U.S. Cl. .................... 514/579; 514/654; 514/655; 514/657; 514/660; 564/374; 564/387; 564/389; 564/391; 428/442; 428/443; 428/457
[58] Field of Search ............... 564/378, 384, 462, 374, 564/387, 389, 391, 428, 442, 443, 457; 514/579, 654, 655, 657, 660

[56] References Cited

U.S. PATENT DOCUMENTS

| | | | |
|---|---|---|---|
| 1,845,563 | 2/1932 | Schmidt et al. | 564/462 X |
| 2,192,927 | 3/1940 | Morrill | 564/384 X |
| 3,842,179 | 10/1974 | Bordenca et al. | 564/384 X |
| 3,882,179 | 5/1975 | Schwam | 424/330 X |
| 4,024,274 | 5/1977 | Druckrey et al. | 564/384 X |
| 4,073,942 | 2/1978 | Keck et al. | 424/330 |
| 4,113,777 | 9/1978 | Keck et al. | 424/330 X |
| 4,822,822 | 4/1989 | Arita et al. | 564/387 X |

FOREIGN PATENT DOCUMENTS 2330454 1/1975 Fed. Rep. of Germany .
489190 7/1938 United Kingdom .

OTHER PUBLICATIONS

The Journal of Organic Chemistry, vol. 48, p. 3412 (1983).

Primary Examiner—Richard L. Raymond
Attorney, Agent, or Firm—Keil & Weinkauf

[57] ABSTRACT 4-trans-substituted cyclohexylamine derivatives of the formula

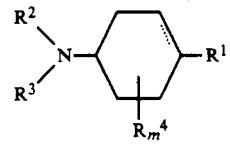

where
$R^1$ is the group $CR^5R^6R^7$, in which $R^5$, $R^6$ and $R^7$ are hydrogen, unsubstituted or substituted alkyl, alkoxy, alkylthio or cycloalkyl, with the proviso that not more than one of the substituents $R^5$, $R^6$ and $R^7$ may by hydrogen, or in which $R^6$ and $R^7$ together with the included carbon atom form a three-membered to six-membered carbocyclic aliphatic ring,
$R^2$ and $R^3$ are hydrogen, alkyl, alkenyl or alkynyl or cycloalkyl or cycloalkenyl, which in turn may be substituted, with the proviso that the sum of the carbon atoms and hetero atoms (O, S and halogen) of $R^2$ and $R^3$ together is not less than 8,
$R^4$ is hydrogen, alkyl, cycloalkyl or alkoxy, and m is 1 to 4, and the ---- bond is a single or a double bond,
salts thereof, and their use as fungicides.

11 Claims, No Drawings

4-SUBSTITUTED CYCLOHEXYLAMINE DERIVATIVES, FUNGICIDES CONTAINING THESE AND A METHOD OF CONTROLLING FUNGI

The present invention relates to 4-substituted cyclohex(en)ylamine derivatives and processes for their preparation, their use as fungicides, fungicidal mixtures, and methods of controlling harmful fungi with these active ingredients.

The compound 4-trans-tert-butyl-N-benzylcyclohexylamine is known (J. Org. Chem. 48 (1983), 3412), but it does not have a significant fungicidal action.

We have found that certain cyclohexylamine derivatives have a powerful fungicidal action coupled with good toleration by plants.

The present invention relates to 4-trans-substituted cyclohexylamines and their derivatives of the formula I

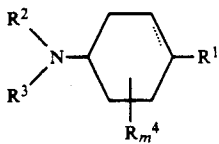

where
- $R^1$ is the group $CR^5R^6R^7$, in which $R^5$, $R^6$ and $R^7$ are identical or different and are each hydrogen, branched or straight-chain, unsubstituted or hydroxyl-substituted $C_1$-$C_8$-alkyl, $C_1$-$C_6$-alkoxy, $C_1$-$C_6$-alkylthio or $C_3$-$C_6$-cycloalkyl, with the proviso that not more than one of the substituents $R^5$, $R^6$ or $R^7$ may be hydrogen, or in which $R^5$ has one of the above meanings and $R^6$ and $R^7$ together with the included carbon atom form a 3-membered to 6-membered carbocyclic aliphatic ring,
- $R^2$ and $R^3$ are identical or different and are each hydrogen, $C_1$-$C_{20}$-alkyl, $C_2$-$C_4$-alkenyl or $C_3$- or $C_4$-alkynyl or $C_3$-$C_{12}$-cyclo-alkyl or $C_5$-$C_8$-cycloalkenyl, which in turn may be substituted by hydroxyl, $C_1$-$C_8$-alkoxy, $C_1$-$C_6$-alkyl-thio, $C_1$-$C_8$-alkyl, $C_2$-$C_4$-alkenyl, $C_3$- or $C_4$-alkynyl or unsubstituted or substitued $C_3$-$C_{12}$-cycloalkyl or by phenyl, naphthyl, phenoxy or naphthyloxy, which in turn may be unsubstituted or substituted by $C_1$-$C_8$-alkyl, $C_2$-$C_4$-alkenyl, $C_3$- or $C_4$-alkynyl or $C_3$-$C_6$-cycloalkyl or $C_5$-$C_8$-cycloalkenyl, $C_2$-$C_8$-alkoxy, halogen or trifluoromethyl, with the proviso that the sum of the carbon atoms and herero atoms (O, S and halogen) of $R^2$ and $R^3$ together is not less than 8,
- the radicals $R^4$ are identical or different substituents in any steric arrangement, selected from the group consisting of hydrogen, $C_1$-$C_8$-alkyl, $C_3$-$C_8$-cycloalkyl and $C_1$-$C_8$-alkoxy and m is 1 to 4, and their salts.

The bond may be a double bond (4-substituted cyclohexenylamine) or a single bond (4-trans-substituted cyclohexylamine).

For practical reasons, salts of the novel amines are also suitable active ingredients.

These include the salts of the amines with any inorganic and organic acids, for example with hydrochloric acid, acetic acid, sulfuric acid, dodecylbenzenesulfonic acid and palmitic acid.

$R^1$ is, for example, $C_3$-$C_8$-alkyl, isopropyl, n-but-2-yl, tert-butyl, n-pent-2-yl, n-pent-3-yl, 2-methyl-but-2-yl, 3-methylbut-2-yl, n-hex-2-yl, n-hex-3-yl, 1,1-dimethylbutyl, n-butyl, heptyl, 2-methylhex-2-yl, n-octyl, 1,1,3,3-tetramethylbutyl, 1-methoxyethyl, 1-ethoxyethyl, 2-methoxyprop-2-yl, 2-ethoxyprop-2-yl, 1-cyclopropylethyl, 1-cyclobutylethyl, 1-cyclopentylethyl, 1-cyclohexylethyl, 2-cyclopropylprop-2-yl, 2-cyclobutylprop-2-yl, 2-cyclopentylprop-2-yl, 2-cyclohexylprop-2-yl, cyclohexen-1-yl, cyclopropyl, cyclobutyl, cyclopentyl, cyclohexyl, cycloheptyl, 1-methylcyclohex-1-yl, 1-ethylcyclohex-1-yl or 4-(4-tert-butylcyclohexyl)-cyclohexyl.

$R^2$ and $R^3$ independently of one another are each, for example, hydrogen, $C_1$-$C_{18}$-alkyl, methyl, ethyl, propyl, isopropyl, n-butyl, isobutyl, n-pentyl, 3-methylbut-2-yl, isopentyl, n-hexyl, n-heptyl, 4,4-dimethylpentyl, n-octyl, 6,6-dimethylhept-2-yl, n-nonyl, 3,5,5-trimethylhexyl, n-decyl, 3,7-dimethyloct-2-yl, n-undecyl, n-dodecyl, n-eicosyl, allyl, propargyl, cyclopropyl, cyclododecyl, 4-tert-butylcyclohexylmethyl, 4-neopentylcyclohexylmethyl, 4-(1,1,3,3-tetramethylbutyl)-cyclohexylmethyl, alkylbenzyl, 4-methylbenzyl, 4-isopropylbenzyl, 4-tert-butylbenzyl, 4-neopentylbenzyl, 4-(1,1,3,3-tetramethylbutyl)-benzyl, trifluoromethylbenzyl, 4-trifluoromethylbenzyl, halobenzyl, 4-chlorobenzyl, 2,4-dichlorobenzyl, 4-methoxybenzyl, 4-tert-butoxybenzyl, 2-chloro-4-phenylbenzyl, α-naphthylmethyl, β-naphthylmethyl, 3-(4-tert-butylphenyl)-2-methylpropyl.

$R^4$, for example, hydrogen, methyl, ethyl, n-propyl, methoxy, ethoxy or cyclohexyl.

m is, for example, 1, 2, 3 or 4.

The novel compounds can be used as fungicides.

The 4-trans-substituted cyclohexylamine compounds are preferred.

The present invention furthermore relates to processes for the preparation of the 4-substituted cyclohex-(en)ylamines of the formula I.

These cyclohex(en)ylamines can be obtained in a conventional manner from corresponding primary amines II

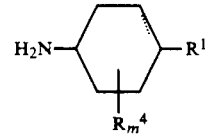

for example by stepwise alkylation.

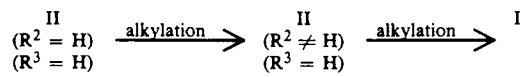

Examples of suitable alkylating agents are appropriate compounds of the type $R^2$-X or $R^3$-X, where X is an electron-attracting leaving group. Instead of the compounds of the above type, in some cases it is also possible to use aldehydes or ketones, these being of the general formulae

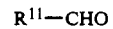

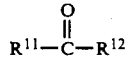

where $R^{11}$ and $R^{12}$ correspond to the radicals $R^2$ and $R^3$, respectively, with the proviso that they contain one carbon atom less than $R^2$ and $R^3$.

The aldehydes and ketones are reacted with the appropriate primary and secondary amines, respectively, in the presence of a reducing agent and in the presence or absence of a catalyst and of a solvent.

In another possible method for the preparation of novel amines, an appropriate imine or iminium salt of the formula

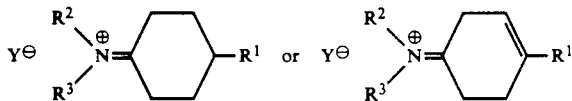

where $Y^\oplus$ is any anion, is reduced stereoselectively to I with a complex hydride in the presence of a diluent.

The primary cyclohexylamines and cyclohexenylamines required as starting materials for the preparation of the novel compounds either are known or are obtainable by, for example, catalytic hydrogenation of appropriate 4-alkyl-substituted nitroaromatics or anilines or reductive amination of 4-alkyl-substituted phenols.

(cf. Methoden der Org. Chemie (Houben-Weyl), Vol. 5/1a, 4th edition, G. Thieme Verlag, Stuttgart 1970. Methoden der Org. Chemie (Houben-Weyl), Vol. 4/1c, 4th edition, G. Thieme Verlag, Stuttgart 1980. Methoden der Org. Chemie (Houben-Weyl), Vol. 11/1, page 108 et seq., 4th edition, G. Thieme Verlag, Stuttgart 1957).

This procedure gives stereoisomer mixtures which can be separated in a conventional manner, for example by distillation.

The compounds of the formulae $R^2X$ and $R^3X$ which are required as starting materials and in which X is chlorine, bromine or iodine or unsubstituted or substituted alkyl- or arylsulfonyloxy, in particular methanesulfonyloxy, trifluoromethanesulfonyloxy or p-toluenesulfonyloxy, are known and many of them are commercial compounds, or they can be prepared from the corresponding alcohols by a conventional method.

Suitable diluents for carrying out alkylation are both protic and aprotic solvents.

These include, in particular, alcohols, such as methanol, ethanol, propanol, butanol or amyl alcohol, aliphatic and aromatic hydrocarbons and halohydrocarbons, e.g. gasoline, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformamilide, N-methylpyrrolidone or hexamethylphosphorotriamide, esters, such as ethyl acetate, and sulfoxides, such as dimethyl sulfoxide. However, it is also possible to dispense with diluents.

The novel process takes place in the presence of an acid acceptor, i.e. an inorganic or organic base. These include, for example, alkali metal hydroxides, such as sodium hydroxide or potassium hydroxide, alkali metal carbonates, such as sodium carbonate, and tertiary amines, such as triethylamine, N,N-dimethylaniline, pyridine, N,N-dimethylaminopyridine or diazobicycloundecene (DBU).

An appropriate excess of the amine being reacted can likewise serve as an acid acceptor and, if the amine is liquid, also as a diluent.

The reaction conditions for such alkylations are known.

This also applies when the novel process is carried out using aldehydes or ketones as starting materials; these too are generally known compounds and many of them are commercially available.

The cyclohexylimines or iminium salts required for carrying out the last-mentioned variant of the process can be prepared from 4-alkyl-substituted cyclohexanones and amines by conventional methods.

(cf.: Methoden der Org. Chemie (Houben-Weyl), Vol. VIII, page 1945 et seq., 4th edition, G. Thieme Verlag, Stuttgart 1952.

Methoden der Org. Chemie (Houben-Weyl), Vol. XI/2, page 77 et seq., 4th edition, G. Thieme Verlag, Stuttgart 1958. Methoden der Org. Chemie (Houben-Weyl), Vol. VII 2b, page 1948 et seq., 4th edition, G. Thieme Verlag, Stuttgart 1976).

The reducing agents used in carrying out the novel process are complex hydrides, preferably sodium borohydride, sodium cyanoborohydride, lithium aluminum hydride, lithium tri-tert-butoxyaluminum hydride or lithium tri-(2-methyl-but-2-yl)-borohydride, and the diluents used are preferably aprotic solvents, such as diethyl ether, tetrahydrofuran, dioxane and ethylene glycol dimethyl and diethyl ether.

Separation of cis/trans-4-tert-butylcyclohexylamine Isomers

About 860 g of isomer mixture are slowly distilled off (about 10–20 drops/min, bp. 205°–208° C.) from 1.5 liters of 4-tert-butylcyclohexylamine (isomer mixture, trans:cis=8:2) under atmospheric pressure over a 100 cm long metal-coated column. 10 g of powdered NaOH are added to the remaining bottom product, and the latter is distilled twice under reduced pressure over a bridge (82° C./11 mbar). A stock of 485 g of trans-4-tert-butylcyclohexylamine (95% of transisomer according to GC and NMR analysis) is obtained and can be used for many of the compounds described below.

EXAMPLE 1 trans-N-(4-tert-butylbenzyl)-4-tert-butylcyclohexylamine 15 mL of 6.5 N methanolic hydrochloric acid are added dropwise to an ice-cooled solution of 15.5 g (0.1 mole) of trans-4-tert-butylcyclohexylamine in 100 ml of absolute methanol. 22 g of molecular sieve (3 A), 16.2 g (0.1 mole) of 4-tert-butylbenzaldehyde and, a little at a time, 3.1 g (50 millimoles) of sodium cyanoborohydride are added, and the mixture is stirred for 22 hours at room temperature. It is acidified with concentrated hydrochloric acid to pH 0–1 and evaporated down under reduced pressure. The solid precipitated is filtered off under suction, washed with methyl tert-butyl ether and treated with 20% of sodium hydroxide solution and methyl tert-butyl ether. The mixture is extracted with methyl tert-butyl ether. The combined organic extracts are washed with water, dried over magnesium sulfate and evaporated down under reduced pressure. The residue obtained is crystallized from hexane at −28° C.

15 g (50% of theory) of the title compound are obtained.

EXAMPLE 2 trans-N-n-Octyl-4-tert-butylcyclohexylamine 26.1 g (0.17 mole) of trans-4-tert-butylcyclohexylamine, 7.7 g (0.056 mole) of potassium carbonate, 4.6 g (0.28 mole) of potassium iodide and 10.8 g (0.056 mole) of n-octyl bromide in 100 ml of acetonitrile are refluxed for 5 hours and evaporated down under reduced pressure, the residue is taken up in dichloromethane and dilute sodium hydroxide solution, and the organic extract is washed, dried over sodium sulfate and evaporated down under reduced pressure. The resulting oil is distilled under reduced pressure.

12.4 g (83%) of the title compound of boiling point 120° C./0.1 mbar are obtained.

The trans-4-substituted cyclohexylamines listed in Table 1 below and the 4-substituted cyclohexen-3-yl-amines listed in Table 2 were prepared in a similar manner, and their properties (physical data and state of aggregation) are stated; the substances listed without such data can be obtained from appropriate intermediates in a similar manner.

TABLE 1

Compounds of the formula I

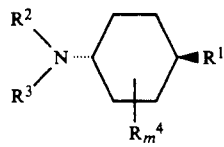

| Compound no. | $R^1$ | $R^2$ | $R^3$ | $R^4$ | State of aggregation, or bp. [°C./mbar] mp. [°C.] |
|---|---|---|---|---|---|
| 3 | tert-butyl | n-butyl | n-butyl | H | oil |
| 4 | " | " | 2-methylethyl | H | oil |
| 5 | " | " | 1,2-dimethylpropyl | H | oil |
| 6 | " | " | 4-methylbutyl | H | oil |
| 7 | " | " | 1,3-dimethylbutyl | H | oil |
| 8 | " | 4,4-dimethylpentyl | methyl | H | oil |
| 9 | " | 4,4-dimethylpentyl | n-butyl | H | oil |
| 10 | " | 1,5-dimethylhexyl | H | H | oil |
| 11 | " | 1,5-dimethylhexyl | methyl | H | oil |
| 12 | " | 1,5-dimethylhexyl | ethyl | H | |
| 13 | " | 1,5-dimethylhexyl | n-propyl | H | |
| 14 | " | 1,5-dimethylhexyl | n-butyl | H | oil |
| 15 | " | 3,5,5-trimethylhexyl | H | H | oil |
| 16 | " | 3,5,5-trimethylhexyl | methyl | H | |
| 17 | " | 3,5,5-trimethylhexyl | ethyl | H | |
| 18 | " | 3,5,5-trimethylhexyl | 2-hydroxyethyl | H | |
| 19 | " | 3,5,5-trimethylhexyl | n-butyl | H | oil |
| 20 | " | 1,2,6-trimethylheptyl | H | H | oil |
| 21 | " | 1,2,6-trimethylheptyl | methyl | H | |
| 22 | " | 1,2,6-trimethylheptyl | ethyl | H | |
| 23 | " | 1,2,6-trimethylheptyl | n-propyl | H | |
| 24 | tert-butyl | 1,2,6-trimethylheptyl | n-butyl | H | oil |
| 25 | " | n-octyl | methyl | H | |
| 26 | " | " | ethyl | H | |
| 27 | " | " | 2-methoxyethyl | H | |
| 28 | " | " | n-butyl | H | oil |
| 29 | " | 3,7-dimethyloctyl | H | H | oil |
| 30 | " | 3,7-dimethyloctyl | methyl | H | oil |
| 31 | " | 3,7-dimethyloctyl | ethyl | H | oil |
| 32 | " | 3,7-dimethyloctyl | isopropyl | H | |
| 33 | " | 3,7-dimethyloctyl | n-butyl | H | oil |
| 34 | " | n-decyl | H | H | oil |

TABLE 1-continued

Compounds of the formula I

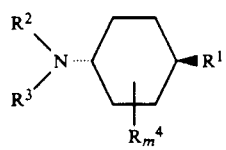

| Compound no. | R¹ | R² | R³ | R⁴ | State of aggregation, or bp. [°C./mbar] mp. [°C.] |
|---|---|---|---|---|---|
| 35 | " | " | ethyl | H | |
| 36 | " | " | 2-methylpropyl | H | |
| 37 | " | " | 1-methylpropyl | H | |
| 38 | " | " | n-butyl | H | |
| 39 | " | 1,5,9-trimethyl-decyl | H | H | oil |
| 40 | " | 1,5,9-trimethyl-decyl | methyl | H | |
| 41 | " | 1,5,9-trimethyl-decyl | ethyl | H | |
| 42 | " | 1,5,9-trimethyl-decyl | n-propyl | H | |
| 43 | " | 1,5,9-trimethyl-decyl | n-butyl | H | oil |
| 44 | " | 4-tert-butylbenzyl | methyl | H | 56–58 |
| 45 | " | 4-tert-butylbenzyl | ethyl | H | oil |
| 46 | " | 4-tert-butylbenzyl | 2-hydroxyethyl | H | |
| 47 | " | 4-tert-butylbenzyl | n-butyl | H | oil |
| 48 | " | 4-tert-butylbenzyl | n-pentyl | H | |
| 49 | " | 4-tert-butylbenzyl | 1-methylethyl | H | oil |
| 50 | tert-butyl | 4-tert-butyl-benzyl | isobutyl | H | |
| 51 | " | 4-tert-butyl-benzyl | 4-methylbutyl | H | |
| 52 | " | 4-tert-butyl-benzyl | 2-hydroxyethyl | H | |
| 53 | " | 4-tert-butyl-benzyl | 2-methoxyethyl | H | |
| 54 | " | 3-(4-tert-butylphenyl) | 2-methylpropyl | H | 72–76 |
| 55 | " | 4-chlorobenzyl | H | H | 53–55 |
| 56 | " | 2,4-dichloro-benzyl | H | H | 68–71 |
| 57 | " | 2-phenoxyethyl | H | H | oil |
| 58 | " | 2-(2,4-dichloro-phenoxy)-ethyl | H | H | 64–68 |
| 59 | " | 9-methylfluoren-9-yl | H | H | oil |
| 60 | " | 5-(4-methyl-phenyl)-pentyl | H | H | 184/0.4 |
| 61 | " | 5-(4-methoxy-phenyl)-pentyl | H | H | 184/0.1 |
| 62 | " | 5-(4-isopropyl-phenyl)-pentyl | H | H | oil |
| 63 | " | 8-(4-methyl-pentyl)-octyl | H | H | 215/0.9 |
| 64 | " | 5-(2,4-dimethyl-phenyl)-pentyl | H | H | 159/0.1 |
| 65 | " | 3-tert-butylbenz-yl | H | H | |
| 66 | " | 4-(2,4-dichloro-phenoxy)-butyl | H | H | |
| 67 | " | 5-(4-phenylphen-yl)-pentyl | H | H | |
| 68 | tert-butyl | 5-(2-chloro-4-phenylphenyl)-pentyl | H | H | |
| 69 | " | 5-(2,4,6-trimethyl-phenyl)-pentyl | H | H | |
| 70 | " | 5-(2,4-dichloro-phenyl)pentyl | H | H | |
| 71 | isopropyl | 5-(4-methylphenyl)-pentyl | H | H | 166/0.1 |

TABLE 1-continued

Compounds of the formula I

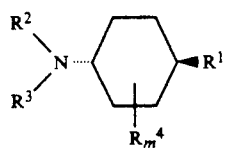

| Compound no. | R¹ | R² | R³ | R⁴ | State of aggregation, or bp. [°C./mbar] mp. [°C.] |
|---|---|---|---|---|---|
| 72 | 2-hydroxy-1,1-dimethyl-ethyl | 4-tert-butylbenzyl | 3-methoxy-propyl | H | |
| 73 | 1,1,3,3-tetramethyl-butyl | 4-tert-butylbenzyl | H | H | 150–152 |
| 74 | 1,1,3,3-tetramethyl-butyl | 4-tert-butylbenzyl | 4-tert-butylbenzyl | H | 231–234 |
| 75 | 1,1,3,3-tetramethyl-butyl | 4-tert-butylbenzyl | —CH₃ | H | |
| 76 | tert-butyl | 3-(2-naphthyl)-2-methylpropyl | H | H | 190/0.3 |
| 77 | " | (4-methylcyclohexyl)-methyl | H | H | |
| 78 | " | 4-isopropylbenzyl | H | H | |
| 79 | " | (trans-4-tert-butylcyclohexyl)-methyl | H | H | 66–68 |
| 80 | " | 1-(trans-4-tert-butylcyclohexyl)-ethyl | H | H | |
| 81 | " | (cis-4-tert-butylcyclohexyl)-methyl | H | H | 72–74 |
| 82 | " | 1-(cis-4-tert-butylcyclohexyl)-ethyl | H | H | |
| 83 | " | 1-(4-tertbutyl-phenyl)-ethyl | H | H | 67–69 |
| 84 | " | 4-tert-amylbenzyl | H | H | oil |
| 85 | " | 4-sec-butylbenzyl | H | H | |
| 86 | " | 4-(1,2-dimethylpropyl)-benzyl | H | H | |
| 87 | " | 4-tert-butoxybenzyl | H | H | 160/0.3 |
| 88 | " | 4-(1,1,3,3-tetramethylbutyl)-benzyl | H | H | |
| 89 | " | 4-butylbenzyl | H | H | |
| 90 | " | 4-butoxylbenzyl | H | H | 170/0.2 |
| 91 | " | (4-methylcyclohexyl)-methyl | —CH₃ | | |
| 92 | " | 4-isopropylbenzyl | —CH₃ | H | |
| 93 | " | (trans-4-tert-butyl-cyclohexyl)-methyl | —CH₃ | H | |
| 94 | " | 1-(trans-4-tert-butylcyclohexyl)-ethyl | —CH₃ | H | |
| 95 | " | (cis-4-tert-butyl-cyclohexyl)-methyl | —CH₃ | H | |
| 96 | " | 1-(cis-4-tert-butylcyclohexyl)-ethyl | —CH₃ | H | |
| 97 | " | 1-(4-tert-butyl-phneyl)-ethyl | —CH₃ | H | |
| 98 | " | 4-tert-amylbenzyl | —CH₃ | H | |
| 99 | " | 4-sec-butylbenzyl | —CH₃ | H | |
| 100 | " | 4-(1,2-dimethylpropyl)-benzyl | —CH₃ | H | |
| 101 | " | 4-tert-butoxybenzyl | —CH₃ | H | |
| 102 | " | 4-(1,1,3,3-tetramethylbutyl)-benzyl) | —CH₃ | H | |
| 103 | " | 4-butoxybenzyl | —CH₃ | H | |
| 104 | " | 4-butoxybenzyl | —CH₃ | H | 46–48 |
| 105 | " | (4-methylcyclohexyl)-methyl | 2-hydroxyethyl | H | |

TABLE 1-continued

Compounds of the formula I

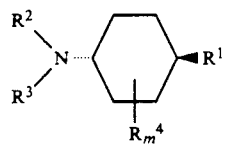

| Compound no. | $R^1$ | $R^2$ | $R^3$ | $R^4$ | State of aggregation, or bp. [°C./mbar] mp. [°C.] |
|---|---|---|---|---|---|
| 106 | " | 4-isopropyl-benzyl | 2-hydroxy-ethyl | H | |
| 107 | " | (trans-4-tert-butylcyclohexyl)-methyl | 2-hydroxy-ethyl | H | |
| 108 | " | 1-(trans-4-tert-butylcyclohexyl)-ethyl | 2-hydroxy-ethyl | H | |
| 109 | " | (cis-4-tert-butyl-cyclohexyl)-methyl | 2-hydroxy-ethyl | H | |
| 110 | " | 1-(cis-4-tert-butylcyclohexyl)-ethyl | 2-hydroxy-ethyl | H | |
| 111 | " | 1-(4-tert-butyl-phenyl)-ethyl | 2-hydroxy-ethyl | H | |
| 112 | " | 4-tert-amylbenzyl | 2-hydroxy-ethyl | H | |
| 113 | " | 4-sec-butylbenzyl | 2-hydroxy-ethyl | H | |
| 114 | " | 4-(1,2-dimethyl-propyl)-benzyl | 2-hydroxy-ethyl | H | |
| 115 | " | 4-tert-butoxybenz-yl | 2-hydroxy-ethyl | H | |
| 116 | " | 4-(1,1,3,3-tetra-methylbutyl)-benzyl | 2-hydroxy-ethyl | H | |
| 117 | " | 4-butylbenzyl | 2-hydroxy-ethyl | H | |
| 118 | " | 4-butoxybenzyl | 2-hydroxy-ethyl | H | |
| 119 | " | (4-methylcyclo-hexyl)-methyl | 2-methoxy-ethyl | H | |
| 120 | " | 4-isopropylbenzyl | 2-methoxy-ethyl | H | |
| 121 | " | (trans-4-tert-butylcyclohexyl)-methyl | 2-methoxy-ethyl | H | |
| 122 | " | 1-(trans-4-tert-butylcyclohexyl)-ethyl | 2-methoxy-ethyl | H | |
| 123 | " | (cis-4-tert-butyl-cyclohexyl)-methyl | 2-methoxy-ethyl | H | |
| 124 | " | 1-(cis-4-tert-butylcyclohexyl)-ethyl | 2-methoxy-ethyl | H | |
| 125 | " | 1-(4-tert-butyl-phenyl)-ethyl | 2-methoxy-ethyl | H | |
| 126 | " | 4-tert-amylbenzyl | 2-methoxy-ethyl | H | |
| 127 | " | 4-sec-butylbenzyl | 2-methoxy-ethyl | H | |
| 128 | " | 4-(1,2-dimethyl-propyl)-benzyl | 2-methoxy-ethyl | H | |
| 129 | " | 4-tert-butoxybenz-yl | 2-methoxy-ethyl | H | |
| 130 | " | 4-(1,1,3,3-tetra-methylbutyl)-benzyl | 2-methoxy-ethyl | H | |
| 131 | tert-butyl | 4-butylbenzyl | 2-methoxy-ethyl | H | |
| 132 | " | 4-butoxybenzyl | 2-methoxy-ethyl | H | |
| 133 | " | (4-methylcyclo-hexyl)-methyl | H | 3-$(CH_3)_2$ | |
| 134 | " | 4-isopropylbenzyl | H | " | |
| 135 | " | (trans-4-tert-butylcyclohexyl)-methyl | H | " | |
| 136 | " | 1-(trans-4-tert- | H | " | |

TABLE 1-continued

Compounds of the formula I

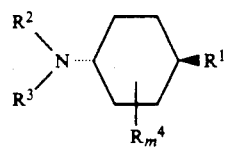

| Compound no. | $R^1$ | $R^2$ | $R^3$ | $R^4$ | State of aggregation, or bp. [°C./mbar] mp. [°C.] |
|---|---|---|---|---|---|
| | | butylcyclohexyl)-ethyl | | | |
| 137 | " | (cis-4-tert-butyl-cyclohexyl)-methyl | H | " | |
| 138 | " | 1-(cis-4-tert-butylcyclohexyl)-ethyl | H | 3-(CH$_3$)$_2$ | |
| 139 | " | 1-(4-tert-butyl-phenyl)-ethyl | H | " | |
| 140 | " | 4-tert-amylbenzyl | H | " | |
| 141 | " | 4-sec-butylbenzyl | H | " | |
| 142 | " | 4-(1,2-dimethyl-propyl)-benzyl | H | " | |
| 143 | " | 4-tert-butoxy-benzyl | H | " | |
| 144 | " | 4-(1,1,3,3-tetra-methylbutyl)-benzyl | H | " | |
| 145 | " | 4-butylbenzyl | H | " | |
| 146 | " | 4-butoxybenzyl | H | " | |
| 147 | tert-amyl | (4-methyl-cyclohexyl)-methyl | H | H | |
| 148 | tert-amyl | 4-isopropyl-benzyl | CH$_3$ | H | |
| 149 | " | (trans-4-tert-butylcyclohexyl)-methyl | 2-hydroxy-ethyl | H | |
| 150 | " | 1-(trans-4-tert-butylcyclohexyl)-ethyl | 2-ethoxy-ethyl | H | |
| 151 | " | (cis-4-tert-butyl-cyclohexyl)-methyl | H | 3-(CH$_3$)$_2$ | |
| 152 | " | 1-(cis-4-tert-butyl-cyclohexyl)-ethyl | H | H | |
| 153 | " | 1-(4-tert-butyl-phenyl)-ethyl | H | H | |
| 154 | " | 4-tert-amylbenzyl | ethyl | H | |
| 155 | " | 4-sec-butylbenzyl | n-butyl | H | |
| 156 | " | 4-(1,2-dimethyl-propyl)-benzyl | H | H | |
| 157 | " | 4-tert-butoxybenzyl | H | H | |
| 158 | " | 4-(1,1,3,3-tetra-methylbutyl)-benzyl | H | H | |
| 159 | " | 4-butylbenzyl | H | H | |
| 160 | " | 4-butoxybenzyl | H | H | |
| 161 | 1,1,3,3-tetramethyl-butyl | (4-methylcyclo-hexyl)-methyl | H | H | |
| 162 | 1,1,3,3-tetramethyl-butyl | 4-isopropylbenzyl | H | H | |
| 163 | 1,1,3,3-tetramethyl-butyl | (trans-4-tert-butylcyclohexyl)-methyl | H | H | |
| 164 | 1,1,3,3-tetramethyl-butyl | 1-(trans-4-tert-butylcyclohexyl)-ethyl | H | H | |
| 165 | 1,1,3,3-tetramethyl-butyl | (cis-4-tert-butyl-cyclohexyl)-methyl | H | H | |
| 166 | 1,1,3,3-tetramethyl-butyl | 1-(cis-4-tert-butylcyclohexyl)-ethyl | H | H | |
| 167 | 1,1,3,3-tetramethyl-butyl | 1-(4-tert-butyl-phenyl)-ethyl | H | H | |
| 168 | 1,1,3,3-tetramethyl-butyl | 4-tert-amylbenzyl | H | H | |

TABLE 1-continued

Compounds of the formula I

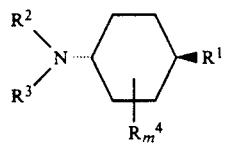

| Compound no. | $R^1$ | $R^2$ | $R^3$ | $R^4$ | State of aggregation, or bp. [°C./mbar] mp. [°C.] |
|---|---|---|---|---|---|
| 169 | 1,1,3,3-tetramethyl-butyl | 4-sec-butylbenzyl | H | H | |
| 170 | 1,1,3,3-tetramethyl-butyl | 4-(1,2-dimethyl-propyl)-benzyl | H | H | |
| 171 | 1,1,3,3-tetramethyl-butyl | 4-tert-butoxy-benzyl | H | H | |
| 172 | 1,1,3,3-tetramethyl-butyl | 4-(1,1,3,3-tetra-methylbutyl)-benzyl | H | H | |
| 173 | 1,1,3,3-tetramethyl-butyl | 4-butylbenzyl | H | H | |
| 174 | 1,1,3,3-tetramethyl-butyl | 4-butoxybenzyl | H | H | |
| 175 | 1-methoxy-1-methyl-ethyl | (4-methylcyclo-hexyl)-methyl | H | H | |
| 176 | 1-methoxy-1-methyl-ethyl | 4-isopropylbenzyl | H | H | |
| 177 | 1-methoxy-1-methyl-ethyl | (trans-4-tert-butylcyclohexyl)-methyl | H | H | |
| 178 | 1-methoxy-1-methyl-ethyl | 1-(trans-4-tert-butylcyclohexyl)-ethyl | H | H | |
| 179 | 1-methoxy-1-methyl-ethyl | (cis-4-tert-butyl-cyclohexyl)-methyl | H | H | |
| 180 | 1-methoxy-1-methyl-ethyl | 1-(cis-4-tert-butylcyclohexyl)-ethyl | H | H | |
| 181 | 1-methoxy-1-methyl-ethyl | 1-(-4-tert-butyl-phenyl)-ethyl | H | H | |
| 182 | 1-methoxy-1-methyl-ethyl | 4-tert-amylbenzyl | H | H | |
| 183 | 1-methoxy-1-methyl-ethyl | 4-sec-butylbenzyl | H | H | |
| 184 | 1-methoxy-1-methyl-ethyl | 4-(1,2-dimethyl-propyl)-benzyl | H | H | |
| 185 | 1-methoxy-1-methyl-ethyl | 4-tert-butoxy-benzyl | H | H | |
| 186 | 1-methoxy-1-methyl-ethyl | 4-(1,1,3,3-tetra-methylbutyl)-benzyl | H | H | |
| 187 | 1-methoxy-1-methyl-ethyl | 4-butylbenzyl | H | H | |
| 188 | 1-methoxy-1-methyl-ethyl | 4-butoxybenzyl | H | H | |
| 189 | tert-amyl | 4-tert-butylbenzyl | H | H | |
| 190 | isopropyl | " | H | H | |
| 191 | cyclohexyl | " | H | H | 68–70 |
| 192 | 1,1,3,3-tetramethyl-butyl | " | 2-hydroxy-ethyl | H | |
| 193 | 1-methoxy-1-methylethyl | " | H | H | |

TABLE 1-continued

Compounds of the formula I

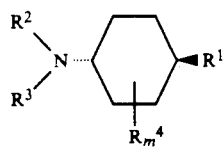

| Compound no. | $R^1$ | $R^2$ | $R^3$ | $R^4$ | State of aggregation, or bp. [°C./mbar] mp. [°C.] |
|---|---|---|---|---|---|
| 194 | 2-hydroxy-1,1-dimethylethyl | " | H | H | |
| 195 | 1,1-dimethylbutyl | " | H | H | |
| 196 | tert-butyl | H | 2-methyl-4-tert butylbenzyl | H | 54–58 |
| 197 | tert-amyl | H | 2-methyl-4-tert butylbenzyl | H | |
| 198 | isopropyl | H | 2-methyl-4-tert butylbenzyl | H | |
| 199 | cyclohexyl | H | 2-methyl-4-tert butylbenzyl | H | |
| 200 | 1,1,3,3-tetramethylbutyl | H | 2-methyl-4-tert butylbenzyl | H | |
| 201 | 1-methoxy-1-methylethyl | H | 2-methyl-4-tert butylbenzyl | H | |
| 202 | 2-hydroxy-1,1-dimethylethyl | H | 2-methyl-4-tert butylbenzyl | H | |
| 203 | 1,1-dimethylbutyl | H | 2-methyl-4-tert butylbenzyl | H | |
| 204 | tert-butyl | H | 4-(1-methoxy-1-methylethyl)-benzyl | H | 47–49 |
| 205 | tert-amyl | H | 4-(1-methoxy-1-methylethyl)-benzyl | H | |
| 206 | isopropyl | H | 4-(1-methoxy-1-methylethyl)-benzyl | H | |
| 207 | cyclohexyl | H | 4-(1-methoxy-1-methylethyl)-benzyl | H | |
| 208 | 1,1,3,3-tetramethylbutyl | H | 4-(1-methoxy-1-methylethyl)-benzyl | H | |
| 209 | 1-methoxy-1-methylethyl | H | 4-(1-methoxy-1-methylethyl)-benzyl | H | |
| 210 | 2-hydroxy-1,1-dimethylethyl | H | 4-(1-methoxy-1-methylethyl)-benzyl | H | |
| 211 | 1,1-dimethylbutyl | H | H | H | |
| 212 | tert-butyl | 2-Cl-4-tert-butylbenzyl | H | H | |
| 213 | tert-amyl | 2-Cl-4-tert-butylbenzyl | H | H | |
| 214 | isopropyl | 2-Cl-4-tert-butylbenzyl | H | H | |
| 215 | cyclohexyl | 2-Cl-4-tert-butylbenzyl | H | H | |
| 216 | 1,1,3,3-tetramethyl-butyl | 2-Cl-4-tert-butylbenzyl | H | H | |
| 217 | 1-methoxy-1-methyl-ethyl | 2-Cl-4-tert-butylbenzyl | H | H | |
| 218 | 2-hydroxy-1,1-dimethyl-ethyl | 2-Cl-4-tert-butylbenzyl | H | H | |
| 219 | 1,1-dimethyl-butyl | 2-Cl-4-tert-butylbenzyl | H | H | |
| 220 | tert-butyl | 2-(4-tert-butyl-phenyl)-ethyl | H | H | oil |
| 221 | tert-amyl | 2-(4-tert-butyl-phenyl)-ethyl | H | H | |
| 222 | isopropyl | 2-(4-tert-butyl-phenyl)-ethyl | H | H | |
| 223 | cyclohexyl | 2-(4-tert-butyl-phenyl)-ethyl | H | H | |
| 224 | 1,1,3,3-tetramethyl-ethyl | 2-(4-tert-butyl-phenyl)-ethyl | H | H | |
| 225 | 1-methoxy-1,1-dimethyl-ethyl | 2-(4-tert-butyl-phenyl)-ethyl | H | H | |
| 226 | 2-hydroxy-1,1-dimethyl-ethyl | 2-(4-tert-butyl-phenyl)-ethyl | H | H | |
| 227 | 1,1-dimethyl-butyl | 2-(4-tert-butyl-phenyl)-ethyl | H | H | |

TABLE 1-continued

Compounds of the formula I

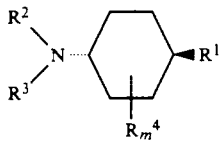

| Compound no. | $R^1$ | $R^2$ | $R^3$ | $R^4$ | State of aggregation, or bp. [°C./mbar] mp. [°C.] |
|---|---|---|---|---|---|
| 254 | tert-butyl | 4-(2-propenyl)-benzyl | H | H | oil |
| 255 | " | 4-(1-hydroxy-1,1-dimethylethyl)-benzyl | H | H | oil |
| 256 | " | 4-methoxy-3-tert.-butyl-benzyl | H | H | 40–42 |
| 257 | " | trans-4-tert.-butyl-cyclohexyl | H | H | 70–72 |
| 258 | " | cis-4-tert.-butyl-cyclohexyl | H | H | 46–48 |
| 259 | " | 2-(2-fluorphenoxy)-ethyl | H | H | oil |
| 260 | " | 2-(2-chlorphenyl)-ethyl | H | H | oil |
| 261 | " | 2-(2,3-dichlorphenyl)-ethyl | H | H | oil |
| 262 | " | 2-(3-trifluormethyl-phenyl)-ethyl | H | H | oil |
| 263 | " | 2-(3-tert.-butyl-phenyl)-ethyl | H | H | oil |
| 264 | tert.-butyl | 3-tert.-butylbenzyl | H | H | oil |
| 265 | 1,1,3,3-tetramethylbutyl | 1-butyl | 1-butyl | H | 150/0.5 |
| 266 | (1-cyclohexyl-1-methyl)-ethyl | 4-tert.-butylbenzyl | H | H | 208–212/0.4 |
| 267 | tert.-butyl | 1-naphthylmethyl | H | H | 175/0.2 |
| 268 | " | 4-trifluormethyl-benzyl | H | H | 127/0.2 |
| 269 | " | 2-brombenzyl | H | H | 146/0.2 |
| 270 | " | cyclopropyl | H | H | oil |
| 271 | " | 4-tert.-butylbenzyl | cyclopropyl | H | oil |
| 272 | " | 2-naphthylmethyl | H | H | oil |
| 273 | " | 3-brombenzyl | H | H | 175/0.9 |
| 274 | " | 4-brombenzyl | H | H | 160/0.5 |
| 275 | " | 3-(2-chlorphenyl)-2-phenyl-2-propenyl | H | H | oil |
| 276 | " | 2-brombenzyl | methyl | H | oil |
| 277 | " | 2-trifluormethylbenzyl | H | H | 138/0.8 |
| 278 | " | 3-brombenzyl | methyl | H | oil |
| 279 | " | 4-brombenzyl | methyl | H | oil |
| 280 | " | n-dodecyl | H | H | 156/0.2 |
| 281 | " | pentafluorbenzyl | H | H | 115/0.2 |
| 282 | " | 2,4,6-trimethylbenzyl | H | H | 178/0.2 |
| 283 | " | 4-n-dodecyl-benzyl | H | H | oil |
| 284 | " | 1-(4-chlorphenyl)-cyclohexyl-1-methyl | H | H | resin |
| 285 | " | 1-(4-chlorphenyl)-cyclohexyl-1-methyl | methyl | H | oil |
| 286 | " | 4-tert.-butylbenzyl | propargyl | H | oil |
| 287 | " | 5-(3,4-dimethyl-phenyl)-pentyl | H | H | 159/0.4 |

TABLE 2

Compounds of the formula

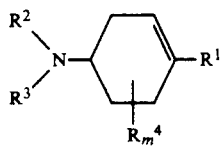

| Compound no. | $R^1$ | $R^2$ | $R^3$ | $R^4$ | State of aggregation, or bp. [°C./mbar] mp. [°C.] |
|---|---|---|---|---|---|
| 228 | tert-butyl | (4-methylcyclo-hexyl)-methyl | ethyl | H | |
| 229 | " | 4-isopropyl-benzyl | methyl | H | |
| 230 | " | (trans-4-tert-butylcyclohexyl)-methyl | H | H | |
| 231 | " | 1-(trans-4-tert-butylcyclohexyl)-ethyl | H | H | |
| 232 | " | (cis-4-tert-butylcyclohexyl)-methyl | 2-hydroxy-ethyl | H | |
| 233 | " | 1-(cis-4-tert-butylcyclohexyl)-ethyl | H | H | |
| 234 | " | 1-(4-tert-butyl-phenyl)-ethyl | H | H | |
| 235 | " | 4-tert-amylbenzyl | H | H | |
| 236 | tert-butyl | 4-sec-butylbenzyl | H | 5-$(CH_3)_2$ | |
| 237 | " | 4-(1,2-dimethyl propyl)-benzyl | H | H | |
| 238 | " | 4-tert-butoxy-benzyl | H | H | |
| 239 | tert-butyl | 4-(1,1,3,3-tetra-methylbutyl)-benzyl | 2-methoxy-ethyl | H | |
| 240 | " | 4-butylbenzyl | H | H | |
| 241 | " | 4-butoxybenzyl | H | H | |
| 242 | " | 4-tert-butyl-benzyl | H | H | |
| 243 | " | 2-methyl-4-tert-butylbenzyl | H | H | |
| 244 | " | 4-(1-methoxy-1-methylethyl)-benzyl | H | H | |
| 245 | " | 2-Cl-4-tert-butyl-benzyl | H | H | |
| 246 | " | 2-(4-tert-butyl-phenyl)-ethyl | H | H | |
| 247 | tert-amyl | 4-tert-butylphenyl | H | H | |
| 248 | isopropyl | " | H | H | |
| 249 | cyclohexyl | " | H | H | |
| 250 | 1,1,3,3-tetra-methylbutyl | " | H | H | |
| 251 | 1-methoxy-1-methylethyl | " | H | H | |
| 252 | 2-hydroxy-1,1 dimethylethyl | " | H | H | |
| 253 | 1,1-dimethyl-butyl | " | H | H | |

USE EXAMPLES

For comparison purposes, N-benzyl-trans-4-tert-butylcyclohexylamine (A; disclosed in J. Org. Chem., 48, 3412, 1983) was used.

EXAMPLE 1

Action on Wheat Mildew

Leaves of pot-grown wheat seedlings of the "Fruh-gold" variety were sprayed with aqueous spray liquors containing (dry basis) 80% of active ingredient and 20% of emulsifier, and dusted, 24 hours after the sprayed-on layer had dried, with spores of wheat mildew (*Erysiphe graminis* var. tritici). The test plants were then set up in the greenhouse at 20° to 22° C. and a relative humidity of 75 to 80%. The extent of mildew spread was determined after 7 days.

In this experiment, a 0.025% formulation of active ingredients 1, 2, 15, 16, 28, 30, 33, 44, 47, 53, 54, 60, 61, 62, 64, 79, 81, 83, 84, 87, 90, 191, 196, 204, 220, 254, 268, 271, 274, 279, 280, 282, 286 and 287 substantially prevented fungus growth, whereas comparative agent A was unable to prevent strong attack and moderate leaf damage (untreated=total attack).

EXAMPLE 2

Action on Cucumber Mildew

Leaves of pot-grown cucumber seedlings of the "Chinesische Schlange" variety were sprayed, at the two-leaf stage, with aqueous conidial suspensions of cucumber mildew. After one day, these plants were sprayed to runoff with aqueous spray liquors containing (dry basis) 80% of active ingredient and 20% of emulsifier, and set up in the greenhouse at from 20° to 22° C. and a relative humidity of 70 to 80%. The extent of fungus attack was assessed 21 days after inoculation.

In this experiment, leaf attack after treatment with a 0.025% formulation of active ingredients 1, 2, 20, 29, 30, 44, 47, 51, 54, 56, 57, 73, 79, 81, 83, 84, 87, 191, 196, 220, 254, 258, 259, 260, 262, 271, 272, 273, 274 and 279 was low, whereas comparative agent A was unable to prevent strong attack and incipient leaf damage (untreated=total attack).

EXAMPLE 3

Action on Wheat Brown Rust

Leaves of pot-grown wheat seedlings of the "Fruhgold" variety were dusted with spores of brown rust (*Puccinia recondita*). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

In this experiment, leaf attack after treatment with a 0.025% formulation of compounds 1, 2, 8, 11, 14, 15, 16, 20, 21, 29, 30, 33, 34, 44, 47, 49, 51, 53, 54, 56, 74, 79, 81, 83, 84, 87, 191, 196, 204, 220, 254, 255, 258, 263, 264, 271, 279 and 282 was low, whereas moderate attack occurred after treatment with comparative compound A (untreated=total attack).

EXAMPLE 4

Action on *Botrytis cinerea* in Pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

In this experiment, leaf attack was low after treatment with a 0.05% formulation of active ingredients 1, 19, 44, 47, 54, 73, 79, 81, 83, 87, 191, 196, 204, 222, 254, 256, 257, 261, 262, 263, 267, 270, 272, 275, 284, 285 and 286 whereas the untreated plants and those treated with the comparative compound suffered total attack.

EXAMPLE 5

Action on *Septoria nodorum*

Leaves of pot-grown wheat seedlings of the "Jubilar" variety were sprayed to runoff with aqueous liquors containing (dry basis) 80% of active ingredient and 20% of emulsifier. On the following day the plants were infected with an aqueous spore suspension of *Septoria nodorum* and further cultivated for 7 days at 17° to 19° C. and a relative humidity of 95%. The extent of fungus spread was then assessed visually.

In this experiment, leaf attack after treatment with a 0.05% formulation of compounds 1, 2, 10, 15, 20, 29, 34, 39, 61 and 73 was low, whereas heavy attack occurred after treatment with the comparative agent and on the untreated plants.

EXAMPLE 6

Action on the Fungi *Paecilomyces variotii*, *Aureobasidium pullulans*, and *Geotrichum candidans*

To test the action on fungi, the active ingredients were added, in amounts of 100, 50, 25, 12, 6, 3 and 1.5 parts per million parts of solution, to a nutrient solution ideally suited for promoting the growth of the fungi *Paecilomyces variotii*, *Aureobasidium pullulans*, and *Geotrichum candidans*. 10 ml of each mixture of nutrient solution and active ingredient was introduced into sterile test tubes and inoculated with one drop of a spore suspension containing $10^6$ conidia or cells. After 120 hours' incubation, samples were taken from those tubes with no visible fungus growth, and transferred to a fungus nutrient medium. The table gives the dilution stage at which, after transfer of a sample to the nutrient medium, fungus growth no longer occurs.

| | Amount of active ingredient (ppm) which is effective | | |
|---|---|---|---|
| Active ingredient | Paecilomyces variotii | Aureobasidium pullulans | Geotrichum candidans |
| 1 | — | 6 | 6 |
| 2 | 12 | 6 | 12 |
| 29 | 3 | 3 | 3 |
| 39 | 6 | 1 | 1 |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaequalis* (scab) in apples,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,

*Pyricularia oryzae* in rice,
*Phytophthora infestans* in potatoes and tomatoes,
*Plasmopara viticola* in grapes, and
Fusarium and Verticillium species in various plants.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (eg., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient.

The application rates are from 0.02 to 3 kg or more of active ingredient per hectare, depending on the type of effect desired. The novel compounds may also be used for protecting materials, for example on *Paecilomyces variotii*, and for combating wood-destroying fungi such as *Coniophora puteana* and *Polystictus versicolor*. The novel active ingredients may also be used as fungicidal components of oily wood preservatives for protecting wood against wood-discoloring fungi. They are applied by treating, for example impregnating or painting, the wood with them.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 15 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 16 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 28 is well mixed with 3 parts by weight of the sodium salt of diisobutylnaphthalene-α-sulfonic acid, 10 parts by weight of the sodium salt of a ligninsulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 30 is intimately mixed with 97 parts by weight of particulate kaolin. A dust is obtained containing 3% by weight of the active ingredient.

VII. 30 parts by weight of compound no. 28 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 44 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 47 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate, ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-5H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

We claim:
1. A 4-transsubstituted cyclohexylamine derivative of the formula

$$\begin{array}{c} R^2 \\ \diagdown \\ N \\ \diagup \\ R^3 \end{array} \!\!\!\!\!\! \diagup\!\!\!\!\!\diagdown \!\!\!\!\!\!\!\! \diagdown\!\!\!\!\!\diagup \!\!\!\!\!\! R^1 \quad R_m^4$$

where
R$^1$ is the group CR$^5$R$^6$R$^7$, in which R$^5$, R$^6$ and R$^7$ are identical or different and are each hydrogen, branched or straight-chain, unsubstituted or hydroxyl-substituted C$_1$–C$_8$-alkyl, C$_1$–C$_6$-alkoxy, C$_1$–C$_6$-alkylthio or C$_3$–C$_6$-cycloalkyl, with the proviso that not more than one of the substituents R$^5$, R$^6$ and R$^7$ may be hydrogen, or in which R$^5$ has one of the above meanings and R$^6$ and R$^7$ together with the included carbon atom form a three-membered to six-membered carbocyclic aliphatic ring,
R$^2$ and R$^3$ are identical or different and are each C$_1$–C$_{20}$-alkyl, C$_2$–C$_4$-alkenyl or C$_3$- or C$_4$-alkynyl or C$_3$–C$_{12}$-cycloalkyl or C$_5$–C$_8$-cycloalkenyl, which in turn may be substituted by hydroxyl, C$_1$–C$_8$-alkoxy, C$_1$–C$_6$-alkylthio, C$_1$–C$_8$-alkyl, C$_2$–C$_4$-alkenyl, C$_3$- or C$_4$-alkynyl or unsubstituted or substituted C$_3$–C$_{12}$-cycloalkyl or by phenyl, naphthyl, phenoxy or naphthyloxy, which in turn may be unsubstituted or substituted by C$_1$–C$_8$-alkyl, C$_2$–C$_4$-alkenyl, C$_3$- or C$_4$-alkynyl or C$_3$–C$_6$-cycloalkyl or C$_5$–C$_8$-C$_2$–C$_8$-alkoxy, halogen or trifluoromethyl; or $R^2$ is hydrogen and $R^3$ is $C_2$–$C_4$-alkenyl or $C_3$- or $C_4$-alkynyl or $C_3$–$C_{12}$-cycloalkyl or $C_5$–$C_8$-cycloalkenyl, which in turn may be substituted by hydroxyl, $C_1$–$C_8$-alkoxy, $C_1$–$C_6$-alkylthio, $C_1$–$C_8$-alkyl, $C_2$–$C_4$-alkenyl, $C_3$- or $C_4$-alkynyl or unsubstituted or substituted $C_3$–$C_{12}$-cycloalkyl or by phenyl, naphthyl, phenoxy or naphthyloxy, which in turn may be unsubstituted or substituted by $C_1$–$C_8$-alkyl, $C_2$–$C_4$-alkenyl, $C_3$- or $C_4$-alkynyl or $C_3$–$C_6$-cycloalkyl or $C_5$–$C_8$-cycloalkenyl, $C_2$–$C_8$-alkoxy, halogen or trifluoromethyl; or $R^2$ is hydrogen and $R^3$ is $C_1$–$C_{20}$-alkyl which is substituted by hydroxyl, $C_1$–$C_8$-alkoxy, $C_1$–$C_6$-alkylthio, $C_1$–$C_8$-alkyl, $C_2$–$C_4$-alkenyl, $C_3$- or $C_4$-alkynyl or unsubstituted or substituted $C_3$–$C_{12}$-cycloalkyl or by phenyl, naphthyl, phenoxy or naphthyloxy, which in turn may be unsubstituted or substituted by $C_1$–$C_8$-alkyl, $C_2$–$C_4$-alkenyl, $C_3$- or $C_3$-alkynyl or $C_3$–$C_6$-cycloalkyl or $C_5$–$C_8$-cycloalkenyl, halogen or trifluoromethyl; with the proviso that the sum of the carbon atoms and hetero atoms (O, S and halogen) of $R^2$ and $R^3$ together is not less than 8, $R^4$ are identical or different substituents selected from the group consisting of hydrogen, $C_1$–$C_8$-alkyl, $C_3$–$C_8$-cycloalkyl and $C_1$–$C_8$-alkoxy, m is 1 to 4, and the bond is a single or a double bond, and salts thereof.

2. The 4-trans-substituted cyclohexylamine derivative of claim 1, wherein the bond is a double bond, said derivative being a 4-trans-substituted cyclohexenylamine.

3. trans-N-(4-tert-butylbenzyl)-4-tert-butylcyclohexylamine.

4. A fungicidal composition containing a 4-trans-substituted cyclohexylamine derivative of the formula

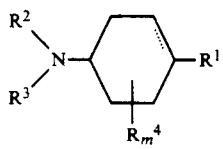

where
$R^1$ is the group $CR^5R^6R^7$, in which $R^5$, $R^6$ and $R^7$ are identical or different and are each hydrogen, branched or straight-chain, unsubstituted or hydroxyl-substituted $C_1$–$C_8$-alkyl, $C_1$–$C_6$-alkoxy, $C_1$–$C_6$-alkylthio or $C_3$–$C_6$-cycloalkyl, with the proviso that not more than one of the substituents $R^5$, $R^6$ and $R^7$ may be hydrogen, or in which $R^5$ has one of the above meanings and $R^6$ and $R^7$ together with the included carbon atom form a three-membered to six-membered carbocyclic aliphatic ring, $R^2$ and $R^3$ are identical or different and are each $C_1$–$C_{20}$-alkyl, $C_2$–$C_4$-alkenyl or $C_3$- or $C_4$-alkynyl or $C_3$–$C_{12}$-cycloalkyl or $C_5$–$C_8$-cycloalkenyl, which in turn may be substituted by hydroxyl, $C_1$–$C_8$-alkoxy, $C_1$–$C_6$-alkylthio, $C_1$–$C_8$-alkyl, $C_2$–$C_4$-alkenyl, $C_3$- or $C_4$-alkynyl or unsubstituted or substituted $C_3$–$C_{12}$-cycloalkyl or by phenyl, naphthyl, phenoxy or naphthyloxy, which in turn may be unsubstituted or substituted by $C_1$–$C_8$-alkyl, $C_2$–$C_4$-alkenyl, $C_3$-or $C_4$-alkynyl or $C_3$–$C_6$-cycloalkyl or $C_5$–$C_8$-cycloalkenyl, $C_2$–$C_8$-alkoxy, halogen or trifluoromethyl; or $R^2$ is hydrogen and $R^3$ is $C_2$–$C_4$-alkenyl or $C_3$- or $C_4$-alkynyl or $C_3$–$C_{12}$-cycloalkyl or $C_5$–$C_8$-cycloalkenyl, which in turn may be substituted by hydroxyl, $C_1$–$C_8$-alkoxy, $C_1$–$C_6$-alkylthio, $C_1$–$C_8$-alkyl, $C_2$–$C_4$-alkenyl, $C_3$- or $C_4$-alkynyl or unsubstituted or substituted $C_3$–$C_{12}$-cycloalkyl or by phenyl, naphthyl, phenoxy or naphthyloxy, which in turn may be unsubstituted or substituted by $C_1$–$C_8$-alkyl, $C_2$–$C_4$-alkenyl, $C_3$-or $C_4$-alkynyl or $C_3$–$C_6$-cycloalkyl or $C_5$–$C_8$-cycloalkenyl, $C_2$–$C_8$-alkoxy, halogen or trifluoromethyl; or $R^2$ is hydrogen and $R^3$ is $C_1$–$C_{20}$-alkyl which is substituted by hydroxyl, $C_1$–$C_8$-alkoxy, $C_1$–$C_6$-alkylthio, $C_1$–$C_8$-alkyl, $C_2$–$C_4$-alkenyl, $C_3$- or $C_4$-alkynyl or unsubstituted or substituted $C_3$–$C_{12}$-cycloalkyl or by phenyl, naphthyl, phenoxy or naphthyloxy, which in turn may be unsubstituted or substituted by $C_1$–$C_8$-alkyl, $C_2$–$C_4$-alkenyl, $C_3$-or $C_3$-alkynyl or $C_3$–$C_6$-cycloalkyl or $C_5$–$C_8$-cycloalkenyl, halogen or trifluoromethyl; with the proviso that the sum of the carbon atoms and hetero atoms (O, S and halogen) of $R^2$ and $R^3$ together is not less than 8, $R^4$ are identical or different substituents selected from the group consisting of hydrogen, $C_1$–$C_8$-alkyl, $C_3$–$C_8$-cycloalkyl and $C_1$–$C_8$-alkoxy, m is 1 to 4, and the bond is a single or a double bond, or a salt thereof, and a solid or liquid carrier.

5. The fungicidal composition of claim 4, wherein the bond in the 4-trans-substituted cyclohexylamine derivative is a single bond 6. The fungicidal composition of claim 4, wherein the bond in the 4-trans-substituted cyclohexylamine derivative is a double bond.

7. A process for combating fungi, wherein a 4-substituted cyclohexylamine derivative of the formula

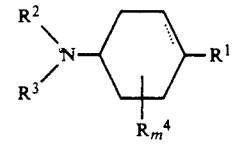

where
$R^1$ is the group $CR^5R^6R^7$, in which $R^5$, $R^6$ and $R^7$ are identical or different and are each hydrogen, branched or straight-chain, unsubstituted or hydroxyl-substituted $C_1$–$C_8$-alkyl, $C_1$–$C_6$-alkoxy, $C_1$–$C_6$-alkylthio or $C_3$–$C_6$-cycloalkyl, with the proviso that not more than one of the substituents $R^5$, $R^6$ and $R^7$ may be hydrogen, or in which $R^5$ has one of the above meanings and $R^6$ and $R^7$ together with the included carbon atom form a three-membered to six-membered carbocyclic aliphatic ring, $R^2$ and $R^3$ are identical or different and are each $C_1$–$C_{20}$-alkyl, $C_2$–$C_4$-alkenyl or $C_3$- or $C_4$-alkynyl or $C_3$–$C_{12}$-cycloalkyl or $C_5$–$C_8$-cycloalkenyl, which in turn may be substituted by hydroxyl, $C_1$–$C_8$-alkoxy, $C_1$–$C_6$-alkylthio, $C_1$–$C_8$-alkyl, $C_2$–$C_4$-alkenyl, $C_3$- or $C_4$-alkynyl or unsubstituted or substituted $C_3$–$C_{12}$-cycloalkyl or by phenyl, naphthyl, phenoxy or naphthyloxy, which in turn may be unsubstituted or substituted by $C_1$–$C_8$-alkyl, $C_2$–$C_4$-alkenyl, $C_3$-or $C_4$-alkynyl or $C_3$–$C_6$-cycloalkyl or $C_5$–$C_8$-cycloalkenyl, $C_2$–$C_8$-alkoxy, halogen or trifluoromethyl; or $R^2$ is hydrogen and $R^3$ is $C_2$–$C_4$-alkenyl or $C_3$- or $C_4$-alkynyl or $C_3$-$C_{12}$-cycloalkyl or $C_5$-$C_8$-cycloalkenyl, which in turn may be substituted by hydroxyl, $C_1$-$C_8$-alkoxy, $C_1$-$C_6$-alkylthio, $C_1$-$C_8$-alkyl, $C_2$-$C_4$-alkenyl, $C_3$- or $C_4$-alkynyl or unsubstituted or substituted $C_3$-$C_{12}$-cycloalkyl or by phenyl, naphthyl, phenoxy or naphthyloxy, which in turn may be unsubstituted or substituted by $C_1$-$C_8$-alkyl, $C_2$-$C_4$-alkenyl, $C_3$-or $C_4$-alkynyl or $C_3$-$C_6$-cycloalkyl or $C_5$-$C_8$-cycloalkenyl, $C_2$-$C_8$-alkoxy, halogen or trifluoromethyl; or $R^2$ is hydrogen and $R^3$ is $C_1$-$C_{20}$-alkyl which is substituted by hydroxyl, $C_1$-$C_8$-alkoxy, $C_1$-$C_6$-alkylthio, $C_1$-$C_8$-alkyl, $C_2$-$C_4$-alkenyl, $C_3$- or $C_4$-alkynyl or unsubstituted or substituted $C_3$-$C_{12}$-cycloalkyl or by phenyl, naphthyl, phenoxy or naphthyloxy, which in turn may be unsubstituted or substituted by $C_1$-$C_8$-alkyl, $C_2$-$C_4$-alkenyl, $C_3$-or $C_3$-alkynyl or $C_3$-$C_6$-cycloalkyl or $C_5$-$C_8$-cycloalkenyl, $C_2$-$C_8$-alkoxy, halogen or trifluoromethyl; with the proviso that the sum of the carbon atoms and hetero atoms (O, S and halogen) of $R^2$ and $R^3$ together is not less than 8, $R^4$ are identical or different substituents selected from the group consisting of hydrogen, $C_1$-$C_8$-alkyl, $C_3$-$C_8$-cycloalkyl and $C_1$-$C_8$-alkoxy, m is 1 to 4, and the ⋯ bond is a single or a double bond, or a salt thereof, is allowed to act on fungi or on materials, areas, plants or seed threatened by fungus attack.

8. The process of claim 7, wherein the 4-substituted cyclohexylamine derivative is a 4-trans-substituted cyclohexylamine derivative, said ⋯ bond being a single bond.

9. The process of claim 7, wherein the 4-substituted cyclohexylamine derivative is a 4-substituted cyclohexenylamine derivative, said bond being a double bond.

10. The process of claim 8, wherein the 4-trans-substituted cyclohexyl derivative is trans-N-(4-tert-butylbenzyl)-4-tert-butylcyclohexylamine.

11. The 4-trans-substituted cyclohexylamine derivative of claim 1 wherein the ⋯ bond in the 4-trans-substituted cyclohexylamine derivative is a single bond.

* * * * *